(12) United States Patent
Cichocki et al.

(10) Patent No.: US 8,808,724 B2
(45) Date of Patent: Aug. 19, 2014

(54) ANTIMICROBIAL COATINGS WITH PREFERRED MICROSTRUCTURE FOR MEDICAL DEVICES

(75) Inventors: Frank Cichocki, Easton, PA (US);
Michael (Jake) Hamilton, Hillsborough, NJ (US); Xintian Ming, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 613 days.

(21) Appl. No.: 12/607,556

(22) Filed: Oct. 28, 2009

(65) Prior Publication Data

US 2011/0098724 A1    Apr. 28, 2011

(51) Int. Cl.
| | | |
|---|---|---|
| *A61F 13/00* | (2006.01) | |
| *A61F 2/00* | (2006.01) | |
| *A01N 25/00* | (2006.01) | |
| *A01N 59/16* | (2006.01) | |
| *A61L 33/00* | (2006.01) | |

(52) U.S. Cl.
USPC ........... 424/423; 424/405; 424/422; 424/618; 427/2.24

(58) Field of Classification Search
USPC .................. 424/405, 422, 423, 618; 427/2.24
See application file for complete search history.

(56) References Cited

U.S. PATENT DOCUMENTS

| | | | |
|---|---|---|---|
| 4,923,619 A | 5/1990 | Legros | |
| 5,681,575 A | 10/1997 | Burrell et al. | |
| 6,224,579 B1 | 5/2001 | Modak et al. | |
| 7,247,338 B2 * | 7/2007 | Pui et al. | 427/2.24 |
| 7,820,284 B2 | 10/2010 | Terry | |
| 2003/0054090 A1 * | 3/2003 | Hansen | 427/2.1 |
| 2005/0085924 A1 | 4/2005 | Darois | |
| 2006/0100278 A1 * | 5/2006 | Cooper et al. | 514/554 |
| 2006/0263329 A1 | 11/2006 | Eemeta | |
| 2006/0263444 A1 | 11/2006 | Ming | |
| 2006/0264347 A1 | 11/2006 | Ming | |
| 2007/0225220 A1 | 9/2007 | Ming | |
| 2007/0292469 A1 | 12/2007 | Rothenburger | |
| 2008/0014144 A1 * | 1/2008 | Saltzman et al. | 424/9.1 |
| 2008/0199506 A1 * | 8/2008 | Horres et al. | 424/423 |
| 2008/0275230 A1 | 11/2008 | Liu | |

FOREIGN PATENT DOCUMENTS

| | | |
|---|---|---|
| CN | 1612804 | 5/2005 |
| EP | 1635850 B1 | 8/2008 |
| WO | WO 0023124 A1 * | 4/2000 |
| WO | 0195876 | 12/2001 |
| WO | WO 2004/056404 A3 | 9/2004 |

* cited by examiner

*Primary Examiner* — Abigail Fisher (74) *Attorney, Agent, or Firm* — E. Richard Skula (57) ABSTRACT

A medical device having an antimicrobial coating. The device has a first coating layer having an antimicrobial agent over at least part of the outer surfaces of the device. The first coating has an outer surface. There is a second discontinuous polymeric coating containing an antimicrobial agent, which is on top of and covering part of the outer surface of the first coating. The second discontinuous coating has a microstructure.

20 Claims, 6 Drawing Sheets

ANTIMICROBIAL COATINGS WITH PREFERRED MICROSTRUCTURE FOR MEDICAL DEVICES

FIELD OF THE INVENTION

The present invention is directed to medical devices having antimicrobial coatings, more particularly medical devices having antimicrobial coatings useful as surgical implants.

BACKGROUND OF THE INVENTION

Non-absorbable, biocompatible polymers play an invaluable role in the surgical treatment and medical care of patients with a variety of ailments. Most commonly, non-absorbable biocompatible polymers are used in a variety of medical devices including sutures, and prosthetic meshes for hernia and pelvic floor repair, wherein at least a portion of these devices remains in the body to provide necessary permanent reinforcement of tissue. Surgical meshes have indeed become the standard of care in hernia repair and pelvic floor repair procedures, providing the necessary strength and structure to reinforce compromised tissues resulting in a permanent tension free repair of the anatomical defect. Turning to surgical wound closure, certain monofilament and braided sutures are comprised of non-absorbable biocompatible polymers and are commonly used to provide permanent fixation for blood vessel anastomosis, heart valve repair, and orthopedic uses including tendon repair and deep tissue closure among other conventional applications and uses.

As with all surgical procedures, surgical wounds incorporating non-absorbable polymer reinforcements, such as sutures or meshes, may be prone to infection. Moreover, it has been long known that non-absorbable implantable materials, even though provided for use in a sterile state, may serve as a nidus for infection by providing a substrate for bacterial attachment, colonization and biofilm formation. Such biofilms, once established, can be extremely resistant to treatment with conventional and available antibiotics and can be life threatening or may otherwise result in protracted long term suffering for the inflicted patient. Infected surgical wounds that have resisted treatment from antibiotics are commonly re-operated upon to access and remove non-absorbable implantable materials and clear the infection before a new prosthetic is implanted to enable the healing process to commence again. Such procedures often require protracted hospital stays, with substantial costs and considerable suffering to the patient as well as the risks attendant with any surgical procedure.

Antimicrobial agents presently used for bioabsorbable polymers may be insufficient for non-absorbable polymer implants. Although it is believed that biofilm formation on bioabsorbable polymers may occur to a lesser degree as well, due to the transient nature of the absorbable polymer substrate supporting the bacterial attachment, these infections are easier to treat and ultimate removal of the bioabsorbable polymers implants are rarely necessary as they will naturally metabolize and leave the body with time. As such, a short-term antimicrobial agent that remains active for durations spanning hours to days may be more acceptable as a prophylactic solution for absorbable implants.

In comparison, with non-absorbable implants if bacteria contamination should survive an initial short acting antimicrobial agent, it would tend to progress and grow unimpeded using surfaces of the non-absorbable implants as an attachment substrate. In such cases, patients when seen by their physicians several weeks to several months after surgery are observed to have indications of infection. It has even been proposed that the initial source of such infection was likely not encountered during the surgical procedure in these cases, but was rather introduced systemically through the circulatory system during a later event. In these scenarios, a short term antimicrobial agent designed to inhibit the growth of bacteria introduced during surgery may be ineffective.

As such, in addition to the potent but short acting antimicrobial effect that may used for bioabsorbable polymer implants, non-absorbable implants may require a long acting efficacy against bacteria colonization and biofilm formation on their surfaces.

The use of combination medical devices that consist of both bioabsorbable and non-absorbable polymeric components is increasing in the medical arts. In particular, hernia meshes that incorporate a bioabsorbable film or fabric on at least one side can be used to inhibit the formation of connective tissue adhesions between internal organs and the surface of the implanted mesh. Since it is known that connective tissue adhesions result in multiple complications, including long term pain, reduction in mobility of patient, and difficulty for the surgeon should future operations be required, these combinational products address an important need. However, when considering surgical site infections, the antimicrobial agent that may be best suited for the bioabsorbable component may not be best suited for the non-absorbable component. For the non-absorbable component, a long-lasting or even permanent antimicrobial surface is desirable for all of the reasons described above. However, for the bioabsorbable component, it may be important that the antimicrobial agent is also bioabsorbable and preferably absorbable at a rate equal to or greater than the absorption rate or degradation rate of the bioabsorbable polymer. In the case of hernia mesh devices, the tissue separating bioabsorbable layer of the mesh can absorb quite rapidly. For example, tissue separating materials such as oxidized regenerated cellulose may absorb and/or degrade within two weeks or less. For these combination products, there is a need for a fast-acting, fast absorbing antimicrobial agent in combination with a long-lasting antimicrobial agent for surface protection for the underlying non-absorbable mesh.

To date, the combination of both a rapidly diffusing antimicrobial agent, that can provide an initial offensive attack against bacteria entrained in the wound during the surgical procedure, and an antimicrobial agent providing long lasting inhibition against bacteria colonization at an implant surface has not been disclosed. Also not disclosed are unique microstructures of such combinational coatings that provide for antimicrobial agents to act effectively and simultaneously from the time of implantation while allowing at least one long term antimicrobial agent to remain attached to the surfaces of the medical device to prevent bacterial attachment for a long term. Furthermore, the use of fast acting, long-ranging antimicrobials (producing a large "zone of inhibition") in the bioabsorbable component of combinational implants along with long-lasting antimicrobials that provide long term protection against surface colonization of the non-absorbable component of the implant has not been described or disclosed.

Therefore, there is a continuing need in this art for novel antimicrobial coatings for implantable medical devices.

SUMMARY OF THE INVENTION

Accordingly, novel medical devices having novel antimicrobial coatings are disclosed. The medical devices have a non-absorbable structure having a surface. A first antimicrobial coating is contained on at least part of the surface of the nonabsorbable structure, the first antimicrobial coating has a coating surface and contains of or contains a first antimicrobial agent, there is a second discontinuous polymeric coating consisting of or containing a second antimicrobial agent. The second coating is applied over at least part of the surface of the first antimicrobial coating. The second discontinuous coating has a microstructure.

Yet another aspect of the present invention is a method of treating a patient using the above-described coated medical devices of the present invention.

Still yet another aspect of the present invention is a method of manufacturing a medical device having an antimicrobial coating.

These and other aspects and advantages of the present invention will become more apparent from the following description and accompanying drawings.

DETAILED DESCRIPTION OF THE INVENTION

The microstructures of the antimicrobial coatings of the present invention provide long term inhibition against bacteria attachment at the surface of the non-absorbable portion or structure of the implant with at least one antimicrobial agent while providing a diffusive longer-ranging antimicrobial release to kill bacteria at a distance away from the surface of the non-absorbable portion of the implant. In this way, both an offensive and a defensive approach to bacteria potentiation may be achieved with protection against bacteria attachment at the device surface provided by the first antimicrobial, and long-range attack on bacteria at a distance away from of the device surface provided by the second antimicrobial release.

In particular, the use of antimicrobial metals in combination with bio-absorbable polymer coatings having antimicrobial agents is described. The antimicrobial metal is used as a first or base coating on at least part of the surfaces of the non-absorbable portion or structure of the implants. The bioabsorbable second coating having a second antimicrobial agent is applied to at least a portion of the surface of the first antimicrobial metallic coating. The second long-ranging antimicrobial agent may be combined with an additional absorbable polymer to facilitate processing, attachment to the implant, and control of release rate from the implant. In an alternate embodiment, when a device is comprised of both absorbable and non-absorbable components or structures, the second long-ranging antimicrobial agent may be incorporated throughout the matrix or onto the surface of the absorbable component of the implantable device.

The term "microstructure" as used herein is defined to have its conventional meaning, for example, the microscopic structure of a material including, phase boundaries, orientations, size scale and surface morphology.

The terms "fast acting" and "long-ranging" antimicrobial agent are defined to mean an antimicrobial agent that diffuses rapidly and provides inhibition against bacterial growth on the order of hours to days, exhibiting a large zone of inhibition wherein bacterial growth is impeded.

The terms "long-lasting" and "short-ranging" "antimicrobial agent are defined to mean an antimicrobial agent that that diffuses slowly and provides inhibition against bacterial growth on the order of days to weeks, exhibiting a profound log reduction against bacterial attachment to the surface even without exhibiting a zone of inhibition.

The term "bioabsorbable polymer" as defined herein is defined to mean a biodegradable or bioabsorbable polymer which degrades or absorbs when in contact with tissue and/or bodily fluids. For example, those polymers that biodegrade via a hydrolysis reaction.

The medical devices that may be coated with the novel two layer coatings of the present invention include any conventional medical devices and equivalents thereof. Such devices typically have a structure. Exemplary devices include, but are not limited to, devices that are implanted or remain in the body or in body tissue such as surgical meshes, surgical sutures, orthopedic implants, bone anchors, pins, or screws, prosthetic vessels, heart valves, pacemakers, and the like. One particularly preferred embodiment of the present invention is to provide the dual layer coatings of the present invention on implantable surgical meshes that are used in various surgical procedures, including for example, hernia repair procedures. The hernia repair devices will preferably consist of both a nonabsorbable component and an absorbable component.

The first coating layer will preferably be applied to substantially all of the outer surfaces of the nonabsorbable component. Although if desired, the first coating layer may be applied to only parts of sections of the outer surfaces of the nonabsorbable component. The nonabsorbable component will typically be made from a conventional biocompatible materials including biocompatible polymers such as polypropylene, polyethylene, polyester, polyethylene terephthalate, polyvinylidene fluouride (PVDF), polytetraflouroethylene, and the like. If desired, the non-absorbable component may be made from other conventional biocompatible materials, including metal alloys, ceramics, composites, etc., and the like.

The first coating layer will consist of or contain a metal or metal alloy. Examples of metals and metal alloys that can be used in the practice of the present invention include, but are not limited to, silver, silver alloys, copper, copper alloys, gold, gold alloys, zinc, zinc alloys, selenium, and the like. If desired, it is possible that the first coating layer is a biocompatible polymer coating containing such metal alloys. Suitable polymer coatings will include polyesters and polyester copolymers, PVP, polyethylene glycols, and the like and combinations thereof. In a particularly preferred embodiment, the metal is applied to at least a portion of the surfaces of the nonabsorbable component by known processes, including physical vapor deposition, chemical vapor deposition, electroplating, and the like. The amount of metal present will be sufficient to effectively coat the uneven surfaces of the implant producing a continuous film and to provide the "long-lasting" and "short-ranging" antimicrobial effect as described above. The thickness of the first coating will be sufficient to effectively uniformly cover the underlying fibers and surfaces of the implant. The coating thickness will typically range from about 20 nm to about 1000 nm, more typically about 20 nm to about 500 nm, and preferably about 50 nm to about 400 nm. When a polymer coating is used for the first coat, conventional coating processes can be similarly used including spraying, dipping, brushing and the like. The thickness of the polymer coating will be sufficient to provide the desired antimicrobial effect, and sufficient to provide effective coverage of the surface. The first antimicrobial coating layer provides a long lasting inhibition against bacteria attachment for a duration in excess of about 14 days post implantation.

As mentioned previously, and in addition thereto, the methods that can be used to apply the first metallic coating to the medical devices of the present invention include physical vapor deposition, chemical vapor deposition, ion implantation, electroplating, or combinations of the above.

The second coating that is applied to the medical devices of the present invention is preferably a polymeric coating containing an antimicrobial agent or agents. The polymeric coating will consist of a conventional biocompatible, biodegradable or bioabsorbable polymer including conventional biodegradable polymers such as polyesters and polyester copolymers, PVP or polyethylene glycols. The biodegradable or bioabsorbable polymers will include lactides, gylcolides, polylactic acid, polyglycolic acid, polycaprolatone, polydioxanone, and copolymers and combinations thereof, as well as equivalents. The antimicrobial agents that may be incorporated into the second coating include conventional antimicrobial agents including LAE, chlorohexidine, octentidine, triclosan and polyhexamethylene biguanide (PHMB), AgI and the like. A sufficient amount of the selected antimicrobial will be incorporated into the second coating to effectively produce a zone of inhibition, extending at least 1 mm from the circumference of the implant, wherein an inhibition against bacteria potentiation is established for a duration of at least one day. The amount will vary depending on the chemical formula and characteristics of the antimicrobial agent, but typically the amounts will be in the range of from about 100 to about 10,000 PPM, more typically about 500 to about 5000 PPM, and preferably about 1000 to about 3000 PPM.

When applied over the outer surface of the first coating, the second coating will be applied in a manner such that it has a discontinuous microstructure. Such a discontinuous microstructure will provide sufficient openings so that a percentage of the surface area of the first coating is exposed. The area of the first coating that is exposed will be sufficient to effectively inhibit bacteria attachment and colonization of the surface of the device. Typically, the exposed area will be about 10% to about 90% of the area of the first coating, more typically about 25% to about 90%, and more typically about 50 to about 90%.

The discontinuous microstructures that can be used in the second coats of the present invention include discrete droplets that form coating islands or sections or areas on the order of 0.1 to 20 um in diameter. A particularly preferred microstructure will have the second coating applied as discrete droplets to form substantially hemispherical-like shapes on the order of 0.1 to 20 um in diameter. The droplets or islands will preferably have a circular, hemispherical or disc configuration upon application although they may have other configurations including substantially elongated ovals, spheres, rods, pyramids, disks, cubes, cylinders, and fibers, and other three-dimensional geometric configurations, including irregular three-dimensional shapes, and combinations thereof. The droplets upon application will have a size of about 0.1 to about 20 um in diameter. It is preferred that adjacent coating droplets or islands be separated by a distance sufficiently effective to allow formation of the discontinuous second layer and allow a sufficient exposure of the surface of the underlying coating to provide for an effective amount of antimicrobial agent produced from first layer when in contact with body fluid. Typically, this distance will be about 1 micron to about 20 micron, more typically about 1 micron to about 10 micron, and preferably about 1 micron to about 2 micron. Although not preferred (and not illustrated), the top or second coating may have a microstructure that is in the form of a continuous coating having open pores that expose the underlying first or base coat. The pores will have an area sufficiently effective to allow formation of the discontinuous microstructure of the second coating layer and allow for an effective amount of the area of the underlying first coat to be exposed to provide for an effective amount of antimicrobial agent to be available from first layer when in contact with body fluid. The microstructure of the second coating is substantially equivalent to that of a bacteria. The surface coverage of the solidified droplets on the surface of the first coating layer ranges from about 1% to 70%.

Typically the area of each pore will be about 1 micron$^2$ to about 4 micron$^2$, more typically about 1 micron$^2$ to about 100 micron$^2$ and preferably about 1 micron$^2$ to about 400 micron$^2$. The total area of the pores will be about 1% to about 90% of the underlying first coating, more typically about 10% to about 50%, and preferably about 15% to about 30%.

The thickness of the second coating will be sufficient to effectively contain and make available a potent dose of the second antimicrobial while not inhibiting the handling characteristics of the prosthetic. Typically, the coating thickness will be about 20 um or less, although thicker coatings may be used depending upon characteristics such as the nature and type of substrate materials, the construction of the device, the type of first coating used, etc.

The second coating may be applied in a variety of conventional ways to obtain a discontinuous coating having the desired microstructure and thickness. Such methods include the following: microspray coating (as may be accomplished with conventionally available spray coating units, ink jet spray coating, printing processes, electrostatic spray coating, etc.

Figure 1:
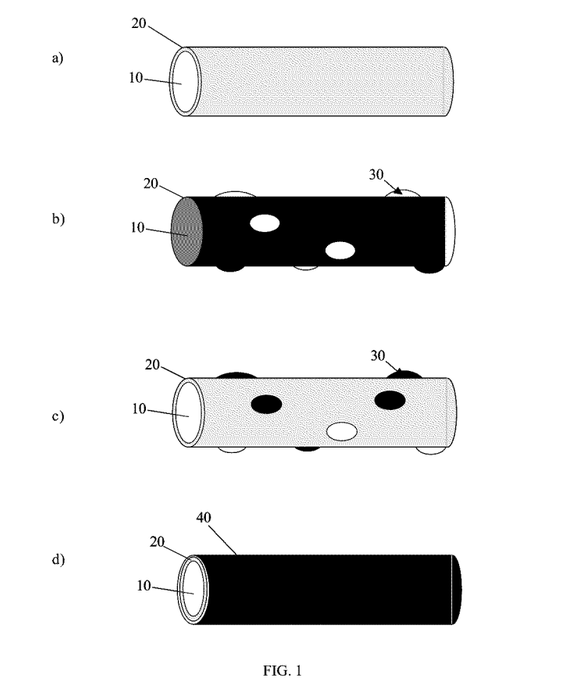
FIGS. 1a-d are schematic depictions of the microstructure of various antimicrobial coatings.
Figure 5:
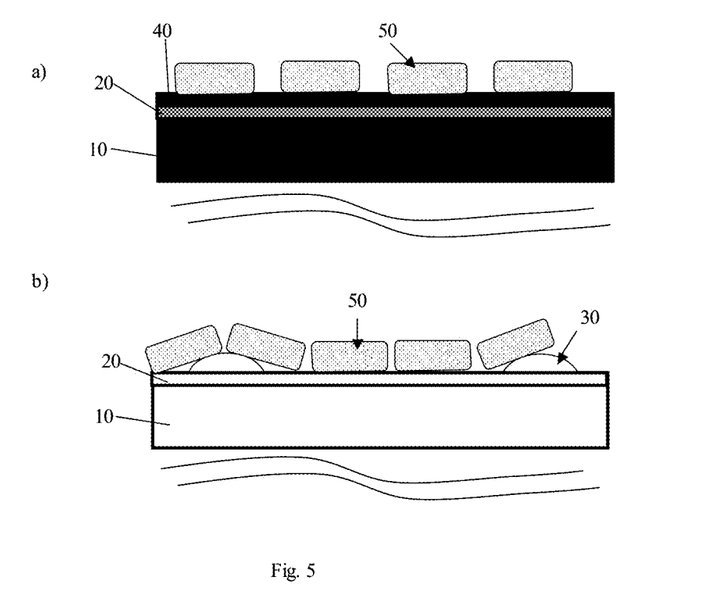
FIGS. 5a and 5b are schematic depiction of bacteria attached to antimicrobial surfaces having differing microstructures.

Referring now to FIGS. 1A-D, a fiber 10 of a mesh device is illustrated. As seen in FIG. 1A, the fiber 10 is seen to have an outer surface 11. The fiber 10 is seen to have an antimicrobial first or base coating layer 20 on outer surface 11. Antimicrobial first coating layer 20 is seen to have outer surface 21. The fiber 10 of FIG. 1B is seen to have the second coating layer 30 applied directly to the surface 11 of fiber 10 (i.e., the first coating 20 is not present), such that the second coating has a microstructure of discrete and discontinuous microstructures 31. Referring now to FIG. 1c, the fiber 10 is seen to have first coating 20 applied to surface 11, and second discontinuous coating 30 applied to surface 21 having a microstructure of discrete, discontinuous droplets or structures 31. FIG. 1d illustrates a fiber 10 having a first coating 20 applied over surface 11 and a second coating 40 applied over surface 21 that is not discontinuous such that none of surface 21 is exposed. FIGS. 5a and 5b are illustrations of coated fiber surfaces having bacteria attached. These FIGS. are further described hereinbelow. The mesh has filaments and fibers. The first antimicrobial coating layer provides a substantially continuous coverage of the filaments and fibers.

The coated medical devices of the present invention may be used in a variety of conventional surgical procedures and equivalents thereof. The procedures include but are not limited to, hernia repair, joint replacement, ligations, facial reconstruction, breast augmentation and the like.

The following examples are illustrative of the principles and practice of the present invention.

Description of Antimicrobial Efficacy Evaluation:

1. Bacteria Attachment Reduction Assay

Bacteria attachment is the first step for biofilm formation and thus infection. Evaluating a prototype mesh for bacteria attachment in vitro would provide a relatively direct indication for biofilm resistance property of the mesh. The in vitro attachment assay was performed in medium SST that contain 20% new born calf serum (heat inactivated, sterile-filtered FCS, Lot #057K8416), 10% TSB (tryptic soy broth) and 70% saline. The media were inoculated with *S. aureus* ATCC 6538 at about 1×10e6 CFU/ml and were incubated in an incubator shaker (12400, New Brunswick, N.J. USA) with rotation of 60 rpm for 24 hr at 37° C. After the incubation, mesh sample was washed to remove unattached cells. The colonized bacteria were removed and homogenized by sonication and were enumerated by agar pour plate methods using TSA agar containing Tween 80 (2.5 mL/L) and lecithin (0.35 g/L). Dilution and plating media contain neutralizing agents were used to eliminate any carry over effect from antimicrobials in coating. The plates were incubated at 37° C. for 24 hours. The number of attached viable organisms was determined by plate count and reported as CFU/mesh. Bacteria attachment log reduction was defined as Log CFU from control mesh–log CFU from treated mesh. For long term efficacy, mesh samples were soaked in sterile saline at 37° C. for a given time and than subject to the attachment assay.

2. Zone of Inhibition Assay

A zone of inhibition assay measures the long ranging efficacy of the antimicrobial component, which produce fast and potent efficacy. In this assay, challenge bacteria were spray inoculated onto surface of TSA plates (tryptic soy agar) at about 5 log CFU/plate. The test article was placed on the surface of the inoculated plate with sterile tools. The plates were incubated at 37° C. for 24-48 hr. A clear no-growth zone around test articles was identified as zone of inhibition and was defined as the average distance in mm from the edge of the test article to the edge of the zone of inhibition.

Example 1

Figure 2:
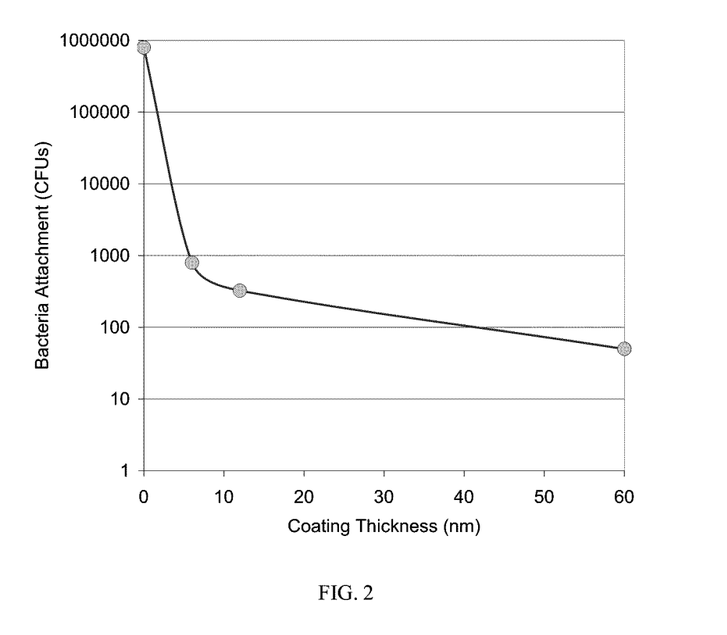
FIG. 2 is a graph of attached bacteria (CFU) count vs. silver coating thickness.

Antimicrobial coatings were applied to a hernia repair mesh comprised of a plurality of polypropylene woven fibers and marketed under the name of Prolene Soft Mesh™ (PSM), by Ethicon Inc. Somerville, N.J., USA. The surfaces of the polypropylene fibers that comprise the PSM were first coated with silver in metallic form via a physical vapor deposition process referred to as sputter coating. The duration of the deposition process was varied to produce metallic silver coatings on the mesh fibers with a variety of thicknesses from about approximately 6 nm to about 60 nm. A schematic depiction of the cross-section of a silver coating, 20, on polypropylene fiber, 10 is shown in FIG. 1a. To gauge the thickness of the coatings, glass slides that were in part covered with a removable tape were sputter coated along side of the mesh samples. Upon completion of the sputtering process, the tape was removed from the glass slide and a profilometer was used to measure the step thickness of the silver on the slide. This approach was particularly effective for estimating silver film thickness on the order of 60 nm or greater. A correlation between film thickness and sputter coating duration was then made from these trials to estimate film thickness less than 60 nm. In order to gain an understanding of the effectiveness of the silver coatings alone prior to combining them with other antimicrobial agents, the meshes were tested for bacteria attachment log reduction and zone of inhibition according to the procedures described above. Results, as a function of estimated film thickness, for mesh samples exposed to *S. aureus* are shown in FIG. 2. About 3 log of bacteria attachment reduction was achieved at silver film thickness of only ~6 nm while a 4 log bacteria attachment reduction was achieved at a film thickness of ~60 nm.

Example 2

Figure 3:
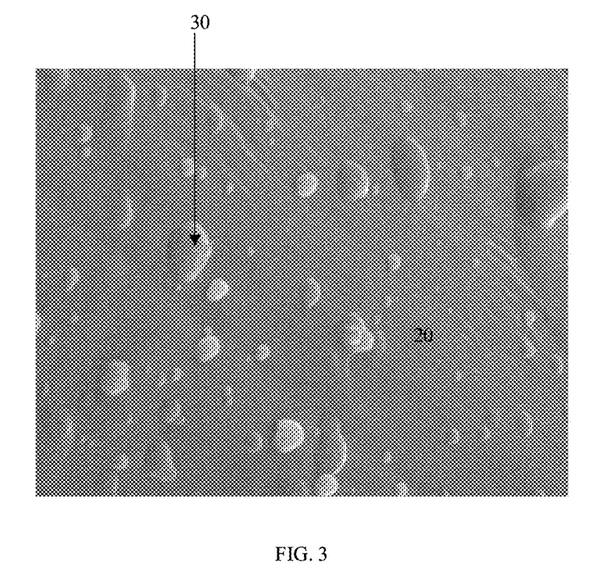
FIG. 3 is a scanning electron micrograph of the combinational antimicrobial coating (triclosan plus silver) schematically depicted in FIG. 1c.

A second antimicrobial agent was applied to the silver coated Prolene Soft Mesh samples produced as described in Example 1. Triclosan was combined with a polylactide-glycolide copolymer comprised of 65% lactide and 35% glycolide, PLA/PGA 65/35. To facilitate processing and microstructure control, about 2.o wt. % of triclosan was combined with the about 4.5 wt. % of PLA/PGA copolymer resin in an ethyl acetate solvent. This solution was then spray-coated onto the mesh using automated microspray equipment produced by Asymtek (A Nordson Company, Amhesrt, Ohio, USA). Mesh samples were weighed before and after application of the spray coatings to determine concentration of triclosan in the film. Concentration of triclosan for samples produced in this study was maintained between approximately about 700 and about 900 ppm. By varying the process parameters of the microspray coater and the formulation ratio of the triclosan-copolymer solution, the microstructure of the triclosan-copolymer coating was adjusted. The microstructures produced were characterized as: 1) "discontinuous triclosan", schematically depicted in FIG. 1b, where discontinuous triclosan containing droplets 30 produced in the spray process have solidified on the polypropylene fiber substrate 10, 2) "silver plus discontinuous triclosan", schematically depicted in FIG. 1c, where discontinuous triclosan containing droplets 30 produced in the spray process have solidified on the metallic silver first coat 20, and 3) "silver plus continuous triclosan" where a continuous triclosan containing coating 40 has been applied to the metallic silver undercoat. A scanning electron micrograph of the "silver coated discontinuous triclosan" sample is shown in FIG. 3. The triclosan copolymer mixture is clearly evident as solidified droplets on the surface of the silver coated polypropylene fiber.

The mesh samples described above were tested for bacteria attachment log reduction and zone of inhibition per the previously described methods. In this sample set, the silver film thickness was estimated as about 6 nm in thickness. Results of this study are presented in FIG. 4. Samples coated with a discontinuous microstructure triclosan containing copolymer alone demonstrated 1.1 log bacteria attachment reduction. Unexpectedly, samples with a metallic silver first coat and a continuous triclosan containing polymer second coat, despite having 2 antimicrobials, performed similarly with a bacteria attachment log reduction of 1. However, a substantially greater reduction in bacteria attachment was exhibited by the "silver plus discontinuous triclosan" samples with a bacteria attachment Log reduction of 2.3.

Schematic representations of the coated fiber surfaces 11 with bacteria 50 attached are shown in FIGS. 5a and b. In FIG. 5a bacteria 50 attempt to attach directly to the continuous triclosan-containing copolymer coating layer 40. In this case, the surface 21 of first silver undercoat or base coat 20 is masked by the continuous antimicrobial (e.g., triclosan) containing top coat 40 and as such silver (or other antimicrobial in coating 20) cannot inhibit bacteria attachment until the copolymer top coat 40 begins to break down and absorb. In FIG. 5b, the triclosan containing copolymer coating 30 is discontinuous (i.e., has a discontinuous microstructure) on a scale comparable to the size of the individual bacteria 50. As such, the bacteria 50 may be exposed to both the base coat and the antimicrobial (e.g., silver) and triclosan containing copolymer at the same time. This is important for several reasons. Firstly, in this case, the silver or first antimicrobial, while potentially short ranging, may be more effective at reducing bacteria attachment than the triclosan active (i.e., the antimicrobial in the top discontinuous coat). Indeed, the fact that the "silver plus discontinuous triclosan" sample performed better than the "silver plus continuous triclosan" sample in the bacteria attachment assay presented in FIG. 4, supports this premise. Secondly, the triclosan phase is transient and may in short order diffuse out of the copolymer coating before the copolymer coating itself absorbs. In this case, the silver may be masked by a copolymer devoid of an antimicrobial agent and bacteria growth may occur. Finally, the synergistic effects that may be realized through the combination of the two different antimicrobial agents are more likely to occur in the latter case where the top antimicrobial coating is discontinuous as this microstructure enables simultaneous release of both silver and triclosan.

Figure 6:
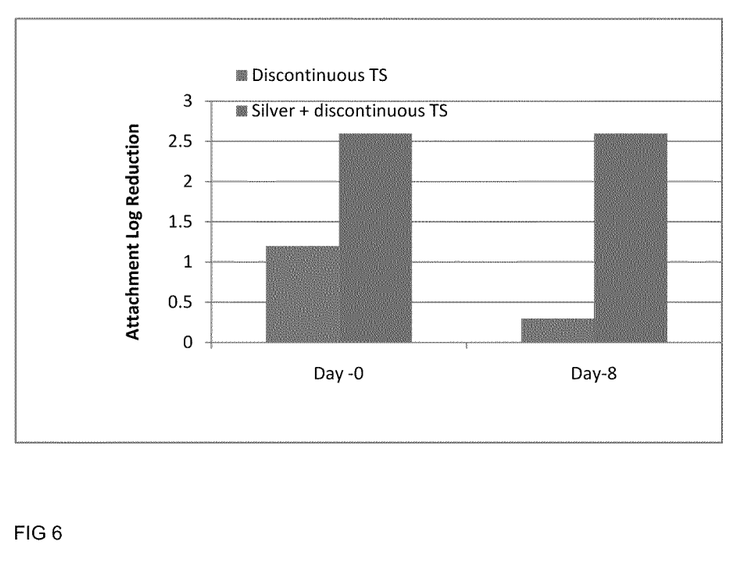
FIG. 6 is a graph showing long term efficacy by attachment log reduction by triclosan-silver combination coated mesh as compared to triclosan alone coated mesh with a similar microstructure.
Figure 7:
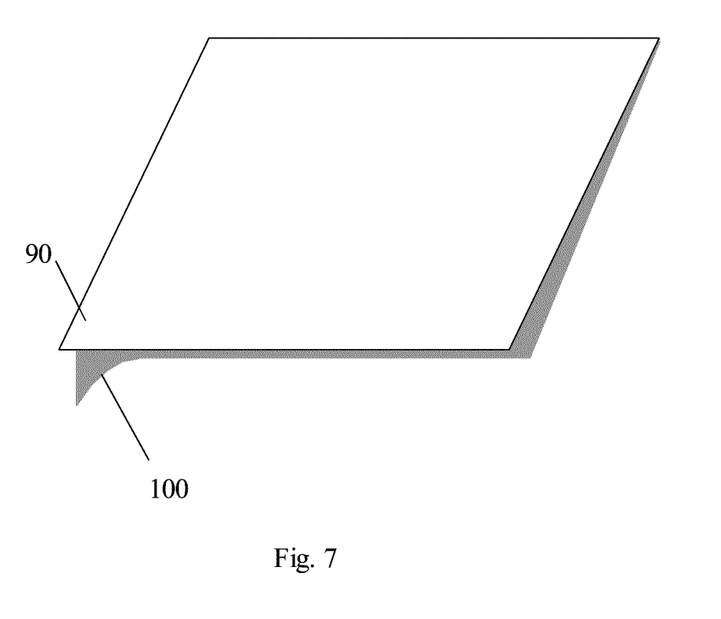
FIG. 7 is a schematic representation of a tissue separation mesh wherein the non-absorbable section is coated with a coating layer having a long-term antimicrobial and a fast acting antimicrobial, and the bioabsorbable section is coated with a coating layer having the fast acting antimicrobial agent or otherwise contains the fast acting antimicrobial agent.
Figure 8:
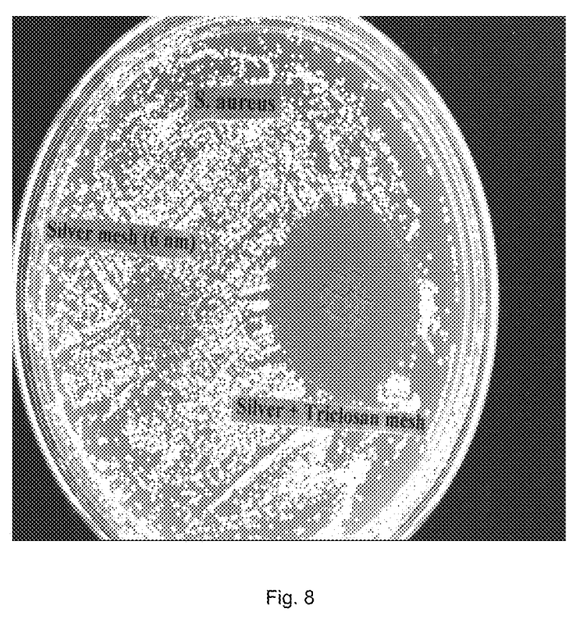
FIG. 8 is a graph showing zone of inhibition against *S. aureus* by silver-coated mesh and silver plus triclosan combination mesh with microstructure

It is important to note that while the reduction in bacteria attachment at the surface of the implant is important and certainly one objective of this invention, it is also proposed that an offensive, fast-acting and long-ranging antimicrobial action away from the surface of the implant is important for preventing infection as well. The zone of inhibition assay and long term efficacy by attachment log reduction assay against *S. aureus* were used to compare the long lasting and, long-range efficacy of triclosan coated, silver coated and "silver plus triclosan" coated mesh samples. FIG. 8 shows the long ranging efficacy by silver plus discontinued triclosan in comparison of short ranging silver coated mesh. FIG. 6 shows the long term efficacy of silver plus discontinued triclosan in comparison with mesh coated with triclosan alone. The triclosan-copolymer discontinuous coating provided a substantially improved zone of inhibition over the sample coated with silver alone as shown in FIG. 8. In addition, it exhibited a long term efficacy over mesh coated with triclosan alone with similar discontinuous microstructure as shown in FIG. 6.

Figure 4:
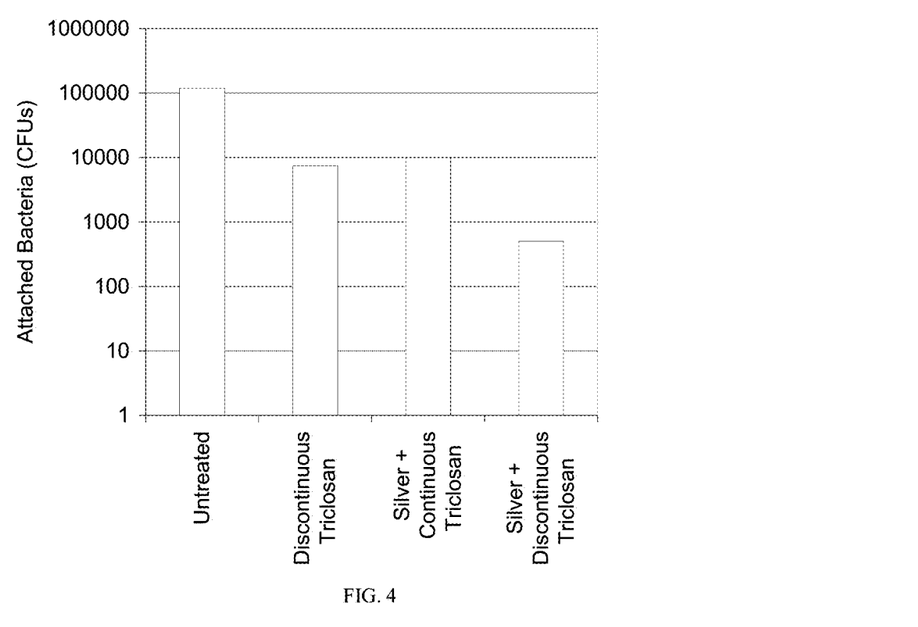
FIG. 4 is a graph showing a comparison of attached bacteria (CFUs) count for triclosan plus silver antimicrobial combination coated implantable mesh samples having varying microstructures.

In order to meet the objective of providing an offensive fasting-acting and long ranging antimicrobial effect, combined with a long-lasting inhibition against bacterial attachment at the device surface, both metallic silver and triclosan in discontinuous form were necessary. Indeed this was the only sample combination that provided a substantial reduction in bacteria attachment along with an effective zone of inhibition as shown in FIGS. 4 and 6 respectively. However, other long-term antimicrobials including but not limited to metallic gold and copper, may be used instead of the silver as the first conformal antimicrobial coating of the non-absorbable implant. Likewise other discontinuous fast-acting, long-ranging antimicrobials that produce a zone of inhibition may be used in lieu of triclosan, including, but not limited to: chlorohexadiene, lauryl acetate, octinedine, and the like. Furthermore, it should be noted that the concept of achieving a fast-acting long ranging antimicrobial effect in combination with inhibition against bacteria adhesion at the device surface may also be obtained with a single antimicrobial agent that is mixed with a slow absorbing or even non-absorbing polymer and applied as a base-film to the implant. A subsequent top-film containing an antimicrobial agent that is mixed in with a fast absorbing polymer, or even alone with no additional polymer, may be applied over the base coat. These coatings may be optimally applied according to the schematic representations in FIGS. 1c and 1d, but most preferably according to FIG. 1c for the same reasons described above.

In the case of implants that are comprised of non-absorbable and absorbable components, especially by way of example, tissue separating hernia meshes with bioabsorbable films or fabrics bonded to at least one side of the non-absorbable component, an offensive fast-acting and long-ranging antimicrobial effect combined with a long lasting inhibition against bacterial attachment at the surfaces of the non-absorbable component may be achieved by incorporating the fast-acting absorbable antimicrobial in the absorbable film itself. This construct may be particularly important for those implants where the absorbable film surrounds or encapsulates at least in part the non-absorbable component, as in the case of tissue separating mesh products used in hernia repair procedures.

Example 3

A patient is prepared in a conventional manner for an open bow resection surgical procedure. A surgical mesh coated with the two layer antimicrobial coatings of the present invention is utilized as an implant for incisional hernia repair. The surgical procedure is conducted as follows. Patient presents with a defect in large bowel that must be removed via open surgery. Post preparation the large bowel is accessed anteriorly through an incision through the peritoneal cavity where the piece of large bow is resected and bowel anastomosis performed. The closure of the incisional hernia is performed by the use of an adhesion reducing hernia mesh placed intraperitoneally and fixed with stay sutures to create a tension free repair of the incisional defect as well as common techniques of fascial, subcuticular and dermal closure.

After successful completion of the repair procedure, the patient is monitored for infection at the following intervals and in the following manner. Due to the inherent nature of bowel resection, the field in which the operation was performed could become contaminated with bowel excretion. Further, it is known that in any procedure the potential for contamination is present. The patient is administered a systemic does of prophylactic antibiotics and then moved to a recovery room for the duration of 4 days. The patient's vital signs are monitored continuously and the repair site is monitored regularly for redness, irritation and other signs of infection. The patient is observed to display no signs of infection four days post operation.

The medical devices of the present invention having novel antimicrobial coatings have many advantages. The advantages include the devices ability to inhibit bacterial colonization of the implant. The devices ability to create a zone around the implant which for a short duration is bactericidal. The ability of the implant to inhibit bacterial colonization for a period longer than a few hours or days. The ability of the implant to inhibit colonization of the implant and simultaneously create a zone around the implant which for some duration is bactericidal. These advantages are all achieved while not compromising the intended use of the device or its specific or unique functions.

Although this invention has been shown and described with respect to detailed embodiments thereof, it will be understood by those skilled in the art that various changes in form and detail thereof may be made without departing from the spirit and scope of the claimed invention.

We claim:

1. A medical device, comprising:
a non-absorbable structure having a surface; and a coating consisting of a first long lasting, short-ranging antimicrobial coating and a second fast acting, long-ranging discontinuous polymeric antimicrobial coating wherein the first long lasting, short-ranging antimicrobial coating is on at least part of the surface, said first antimicrobial coating having a coating surface and comprising a first long-lasting and short-ranging antimicrobial agent; and, the second fast acting, long-ranging discontinuous polymeric antimicrobial coating comprising a second antimicrobial agent, wherein said second antimicrobial coating is applied over at least part of the coating surface of the first antimicrobial coating such that it has a microstructure, and wherein the microstructure of the second discontinuous coating comprises discrete sections, each section having a substantially geometric shape, wherein the second coating comprises a bioabsorbable polymer, and wherein the microstructure of the second coating is substantially equivalent to the length of a bacteria.

2. The medical device of claim 1, wherein the second polymeric discontinuous coating comprises a microstructure that does not prevent bacteria or other microbes from coming in direct contact with the first antimicrobial coating over at least part of the length of the bacteria or microbes.

3. The medical device of claim 1, wherein said first antimicrobial coating layer provides a long lasting inhibition against bacteria attachment for a duration in excess of 14 days post implantation.

4. The medical device of claim 1, wherein the antimicrobial agent in the second discontinuous polymeric coating layer is quickly released from its polymer coating in vivo providing a fast acting and long ranging antimicrobial effect or zone of inhibition against bacteria.

5. The medical device of claim 1, wherein said device comprises a mesh having filaments and fibers.

6. The medical device of claim 5, wherein the first antimicrobial coating layer provides a continuous coverage of the filaments and fibers.

7. The medical device of claim 1, wherein the second discontinuous antimicrobial coating comprises discrete droplets.

8. The medical device of claim 7, where the surface coverage of the solidified droplets on the surface of the first coating layer ranges from about 1% to 70%.

9. The device of claim 1, wherein the first antimicrobial coating layer comprises an antimicrobial metal.

10. The device of claim 9, wherein the antimicrobial metal comprises silver or a silver alloy.

11. The device of claim 1, wherein the discontinuous polymeric coating comprises a bioabsorbable polymer selected from the group consisting of PLA/PGA and PCL/PGA copolymer.

12. The device of claim 1, wherein the second antimicrobial agent is selected from the group consisting of triclosan, chlorohexadine, LAE, AgI, and octenidine.

13. The device of claim 1, wherein the discrete sections have a substantially geometric shape selected from the group consisting of hemispheres, disks, cubes, cylinders, fibers, pyramids, irregular three-dimensional shapes and combinations thereof.

14. The coating of claim 1, wherein the second discontinuous coating is applied by a coating process selected from the group consisting of spraying, printing, and dipping.

15. The medical device of claim 1, wherein the first coating has a first thickness and the second coating has a second thickness.

16. The medical device of claim 1, wherein the distance between the discrete sections is about 1 micron to about 20 microns.

17. The medical device of claim 7, wherein the droplets have a hemispherical shape.

18. The medical device of claim 17, wherein the droplets have a diameter of about 0.1 microns to about 20 microns.

19. A method of performing a surgical repair procedure, comprising:
A. providing the medical device of claim 1;
B. affixing said medical device to a tissue defect within a body cavity to effectively repair the tissue defect.

20. A method of manufacturing the medical device of claim 1, comprising:
providing a medical device comprising a non-absorbable structure having a surface;
applying a first long lasting, short-ranging antimicrobial coating on at least part of the surface, said first antimicrobial coating having a coating surface and comprising a first antimicrobial agent; and, applying a second fast acting, long ranging polymeric coating comprising a second antimicrobial agent, wherein said second coating is applied over at least part of the coating surface of the first antimicrobial coating, such that the second coating has a discontinuous microstructure, and wherein the discontinuous microstructure of the second coating comprises a microstructure having discrete sections, the sections having a substantially geometric shape.

* * * * *